United States Patent [19]

Tanaka et al.

[11] Patent Number: 4,777,267
[45] Date of Patent: Oct. 11, 1988

[54] 1,3-DIOXOL-2-ONE DERIVATIVES

[75] Inventors: Hiroshi Tanaka, Sakai; Mikiya Kitamura, Miriguchi; Fumio Sakamoto, Daito; Masahiro Taguchi, Hirakata; Mikio Sotomura, Kobe, all of Japan

[73] Assignee: Kanebo Ltd., Tokyo, Japan

[21] Appl. No.: 939,711

[22] Filed: Dec. 5, 1986

[30] Foreign Application Priority Data

Feb. 7, 1986 [JP] Japan .................................. 61-26138
Jun. 10, 1986 [JP] Japan ............................... 61-135853

[51] Int. Cl.$^4$ ........................................... C07D 307/58
[52] U.S. Cl. ...................................... 549/229; 435/19
[58] Field of Search ........................................ 549/229

[56] References Cited

U.S. PATENT DOCUMENTS 4,342,693  8/1982  Sakamoto et al. .................. 549/229
4,428,806  1/1984  Sakamoto et al. .................. 549/229

OTHER PUBLICATIONS

English translation of Japanese Kokoku Pat. No. SHO 57-4320.

Primary Examiner—Norma S. Milestone
Attorney, Agent, or Firm—Wenderoth, Lind & Ponack

[57] ABSTRACT

A 1,3-dioxol-2-one derivative represented by the following formula (I)

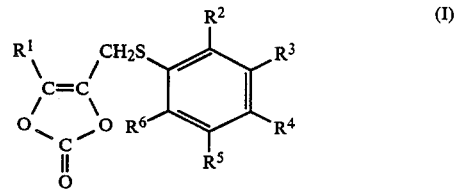

wherein $R^1$ represents a hydrogen atom or an alkyl group having 1 to 4 carbon atoms, $R^2$, $R^3$, $R^4$, $R^5$ and $R^6$ represent independently a hydrogen atom, a halogen atom, an alkyl group having 1 to 4 carbon atoms, an alkoxy group having 1 to 4 carbon atoms, a nitro group, a carboxyl group, salts of the carboxyl group, a sulfo group and salts of the sulfo group, and a process for producing the 1,3-dioxol-2-one derivative. The compound is useful for measuring the activity of arylesterase.

1 Claim, No Drawings

1,3-DIOXOL-2-ONE DERIVATIVES

This invention relates to 1,3-dioxol-2-one derivatives, a process for production thereof, and the use thereof as a substrate for measurement of arylesterase activity. More specifically, it pertains to a new substrate for measurement of arylesterase activity in serum in the diagnosis of liver diseases, particularly liver cirrhosis.

Two different esterases, arylesterase (EC 3.1.1.2; to be abbreviated as ArE hereinafter) and cholinesterase (EC 3.1.1.8; to be abbreviated as ChE), exist in the human blood plasma (cf. Ann. N. Y. Acad., Sci., 94, 844, 1961). It is known that the marked decrease of ArE activity in human serum suggested with high probability the diagnosis of liver cirrhosis [cf. Clin. Chim. Acta., 18, (1967), 21].

ArE activity in serum has heretofore been measured, for example, by a method which comprises hydrolyzing phenyl acetate as a substrate with ArE, and automatically titrating the resulting acetic acid [cf. Clin. Chim. Acta, 18 (1967) 21], a method which comprises reacting phenol simultaneously formed by hydrolysis in the above method, with 4-aminoantipyrine (4-aminophenazone) in the presence of potassium ferricyanide to convert it into 4-(p-benzoquinone-monoimino)phenazone, and colorimetrically, measuring it [cf. Clin. Chem., 25, 1714(1979)], a method which comprises hydrolyzing β-naphthyl acetate as a substrate with ArE, and spectrophotometricallly measuring the resulting β-naphthol [cf. Clin. Chim. Acta, 39, 255 (1972)], or a method which comprises hydrolyzing a thioester as a substrate with ArE, coloring the resultant thiophenol with a SH reagent, and colorimetrically measuring it (cf. Japanese Patent Publication No. 4320/1982).

However, all conventional substrates for measurement of ArE activity are also hydrolyzed by ChE. Therefore, these substrates are not suitable due to their lack of specificity. Hence, when ArE activity in serum is to be measured for diagnosis of liver cirrhosis using a conventional method, it is necessary to obtain ArE fraction by, for example, electrophoretic separation prior to measurement. This makes the overall operation troublesome.

With this background, the present inventors have made extensive investigations in order to find out a new substrate for ArE activity measurement which has high substrate specificity for ArE and excellent sensitivity and accuracy.

It is an object of this invention to provide 1,3-dioxol-2-one derivatives which are novel compounds.

Another object of this invention is to provide the above 1,3-dioxol-2-one derivatives as substrates for measurement of arylesterase.

Still another object of this invention is to provide the above 1,3-dioxol-2-one derivatives which are readily hydrolyzable with ArE but very difficultly hydrolyzable with ChE, and which are useful as substrates for measurement of serum ArE activity in the diagnosis of liver diseases, particularly liver cirrhosis.

Yet another object of this invention is to provide a process for producing the 1,3-dioxol-2-one derivatives of the invention.

Further objects and advantages of this invention will become apparent from the following description.

According to this invention, these objects and advantages of the invention are achieved by a 1,3-dioxol-2-one derivative represented by the following formula (I)

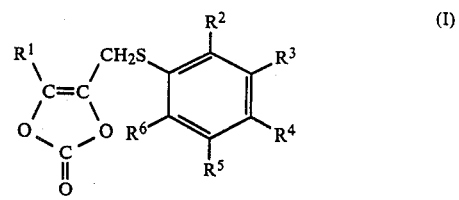

wherein
$R^1$ represents a hydrogen atom or an alkyl group having 1 to 4 carbon atoms,
$R^2$, $R^3$, $R^4$, $R^5$ and $R^6$ represent independently a hydrogen atom, a halogen atom, an alkyl group having 1 to 4 carbon atoms, an alkoxy group having 1 to 4 carbon atoms, a nitro group, a carboxyl group, salts of the carboxyl group, a sulfo group and salts of the sulfo group.

According to this invention, the 1,3-dioxol-2-one derivative of formula (I) can be produced by a process which comprises reacting a compound represented by the following formula (II)

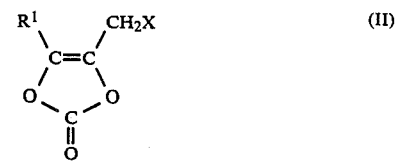

wherein $R^1$ is as defined above, and X represents a halogen atom, with a benzenethiol represented by the following formula (III)

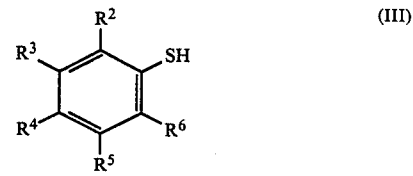

wherein $R^2$, $R^3$, $R^4$, $R^5$, and $R^6$ are as defined above, in the presence of a basic compound.

The compound of formula (II) is known, and can be produced, for example, by the processes described in U.S. Pat. Nos. 4,342,693 and 4,554,358.

$R^1$ in formula (II) is a hydrogen atom or an alkyl group having 1 to 4 carbon atoms. The alkyl group may be liner or branched, and includes, for example, methyl, ethyl, n-propyl, iso-propyl, n-butyl, iso-butyl, sec-butyl and t-butyl. Preferably, $R^1$ is a hydrogen atom or a methyl group, especially the latter.

In formula (II), X is a halogen atom such as chlorine, bromine or iodine. Chlorine or bromine is preferred.

Examples of the compound of formula (II) are
4-chloromethyl-5-methyl-1,3-dioxol-2-one,
4-bromomethyl-5-methyl-1,3-dioxol-2-one,
4-chloromethyl-1,3-dioxol-2-one,
4-bromomethyl-1,3-dioxol-2-one, and
4-bromomethyl-5-n-butyl-1,3-dioxol-2-one.

The compound of formula (III) can be produced by methods known per se.

In formula (III), $R^2$, $R^3$, $R^4$, $R^5$ and $R^6$ represent independently a hydrogen atom, a halogen atom, an alkyl group having 1 to 4 carbon atoms, an alkoxy group having 1 to 4 carbon atoms, a nitro group, a carboxyl group, salts of the carboxyl group, a sulfo group and salts of the sulfo group.

Examples of the halogen atoms are fluorine, chlorine, bromine and iodine, and fluorine and chlorine are preferred.

The alkyl group having 1 to 4 carbon atoms may be linear or branched, and include, for example, methyl, ethyl, n-propyl, iso-propyl, n-butyl, sec-butyl, t-butyl and iso-butyl. Methyl is preferred.

The alkoxy group having 1 to 4 carbon atoms may be linear or branched, and include, for example, methoxy, ethoxy, n-propoxy and n-butoxy. Methoxy is preferred.

The salts of the carboxyl group and the sulfo group are, for example, alkali metal or alkaline earth metal salts of the carboxyl or sulfo group such as Na salts, K salts and Ca salts, and organic amine salts of the carboxyl or sulfo group such as triethylamine salts.

Examples of the compound of formula (III) include
benzenethiol,
2-chlorobenzenethiol,
3-chlorobenzenethiol,
4-chlorobenzenethiol,
2,5-dichlorobenzenethiol,
3,4-dichlorobenzenethiol,
4-fluorobenzenethiol,
2,3,5,6-tetrafluorobenzenethiol,
pentafluorobenzenethiol,
4-bromobenzenethiol,
2-iodobenzenethiol,
2-methylbenzenethiol,
4-methylbenzenethiol,
4-isopropylbenzenethiol,
4-tert-butylbenzenethiol,
2,4-dimethylbenzenethiol,
2,5-dimethylbenzenethiol,
5-isopropyl-2-methylbenzenethiol,
2-methoxybenzenethiol,
4-methoxybenzenethiol,
3-nitrobenzenethiol,
4-nitrobenzenethiol,
2,4-dinitrobenzenethiol,
2-mercaptobenzoic acid,
sodium 4-mercaptobenzoate,
2-mercapto-4-methylbenzoic acid,
2-mercapto-5-methylbenzoic acid,
2-chloro-5-mercaptobenzoic acid,
2-mercaptobenzenesulfonic acid,
3-mercaptobenzenesulfonic acid,
4-mercaptobenzenesulfonic acid,
sodium 3-mercaptobenzenesulfonate, and
triethylammonium 2-mercaptobenzenesulfonate.

The process of this invention is carried out by reacting the compound of formula (II) with the compound of formula (III) in the presence of a basic compound.

Preferably, the reaction is carried out in a non-polar solvent such as dichloromethane. The reaction can be carried out usually at a temperature of 0° to 40° C., and the reaction time is usually about 10 minutes to 4 hours.

In performing the above reaction, 1 mole of the compound of formula (II) and 1 to 1.2 moles of the compound of formula (III) are usually employed. A tertiary amine such as triethylamine is used as the basic compound. The amount of the basic compound is usually 1 to 2.4 moles per mole of the compound of formula (II).

After the reaction, the reaction mixture is worked up in a customary manner to separate and purify the desired product. As a result, the 1,3-dioxol-2-one derivative of the invention represented by formula (I) is obtained.

Examples of the compound of formula (I) provided by this invention include
4-(4-fluorophenyl)thiomethyl-5-methyl-1,3-dioxol-2-one,
4-(2,3,5,6-tetrafluorophenyl)thiomethyl-5-methyl-1,3-dioxol-2-one,
4-(pentafluorophenyl)thiomethyl-5-methyl-1,3-dioxol-2-one,
4-(4-chlorophenyl)thiomethyl-5-methyl-1,3-dioxol-2-one,
4-(2,5-dichlorophenyl)thiomethyl-5-methyl-1,3-dioxol-2-one,
4-(3,4-dichlorophenyl)thiomethyl-5-methyl-1,3-dioxol-2-one,
4-(4-bromophenyl)thiomethyl-5-methyl-1,3-dioxol-2-one,
4-(2-iodophenyl)thiomethyl-5-methyl-1,3-dioxol-2-one,
5-methyl-4-phenylthiomehhyl-1,3-dioxol-2-one,
4-(4-nitrophenyl)thiomethyl-5-methyl-1,3-dioxol-2one,
4-(2,4-dinitrophenyl)thiomethyl-5-methyl-1,3-dioxol-2-one,
4-(4-methylphenyl)thiomethyl-5-methyl-1,3-dioxol-2-one,
4-(5-isopropyl-2-methylphenyl)thiomethyl-5-methyl-1,3-dioxol-2-one,
4-(4-methoxyphenyl)thiomethyl-5-methyl-1,3-dioxol-2-one,
4-(4-fluorophenyl)thiomethyl-1,3-dioxol-2-one,
4-phenylthiomethyl-1,3-dioxol-2-one,
4-(4-nitrophenyl)thiomethyl-1,3-dioxol-2-one,
4-(4-methoxyphenyl)thiomethyl-1,3-dioxol-2-one,
2-chloro-5-[(5-methyl-2-oxo-1,3-dioxol-4-yl)-methylthio]benzoic acid,
5-methyl-2-[(5-methyl-2-oxo-1,3-dioxol-4-yl)-methylthio]benzoic acid,
sodium 2-[(5-methyl-2-oxo-1,3-dioxol-4-yl)-methylthio]benzenesulfonate,
2-[(5-methyl-2-oxo-1,3-dioxol-4-yl)methylthio]benzenesulfonic acid,
Sodium 3-[(5-methyl-2-oxo-1,3-dioxol-4-yl)methylthio]benzenesulfonate,
3-[(5-methyl-2-oxo-1,3-dioxol-4-yl)methylthio]benzenesulfonic acid,
Sodium 4-[(5-methyl-2-oxo-1,3-dioxol-4-yl)methylthio]benzenesulfonate,
4-[(5-methyl-2-oxo-1,3-dioxol-4-yl)methylthio]benzenesulfonic acid,
4-[(5-butyl-2-oxo-1,3-dioxol-4-yl)methylthio]benzenesulfonic acid, and
4-[(2-oxo-1,3-dioxol-4-yl)methylthio]benzenesulfonic acid.

ArE activity of human serum can be determined by subjecting a solution of the compound of this invention as a substrate to enzymatic reaction with a serum sample in a buffer having a pH of 5 to 9, preferably 6 to 8, measuring the initial formation rate of benzenethiol (the rate of hydrolyzing the thioether), or measuring the amount of benzenethiol formed after a certain period of time.

The initial formation rate of benzenethiol or the amount of benzenethiol formed after a certain period of time can be measured colorimetrically by using a SH reagent such as 5,5'-dithiobis(2-nitrobenzoic acid) (DTNB) (cf. Test Examples given hereinafter). If the product is a nitrobenzenethiol derivative such as 4-nitrobenzenethiol which colors by itself, it can be directly measured colorimetrically (for example, at a wavelength of 412 nm).

As shown by the results of tests given hereinafter, the compounds of this invention can be easily hydrolyzed with ArE, but are very difficultly hydrolyzable with ChE. Hence, they are excellent specific substrates for measurement of ArE activity in serum (cf. Table 1), and are useful as substrates for measuring ArE activity in serum for diagnosis of liver diseases, particularly liver cirrhosis (cf. Tables 2 and 3).

TEST EXAMPLE 1

Substrate specificity and reactivity of the compounds of this invention for ArE (i) Test compounds (substrates)

Compounds of this invention obtained in Examples 1 to 14 given hereinafter, phenyl acetate (a control compound produced by Tokyo Chemical Industry Co., Ltd.), β-naphthyl acetate (a control compound produced by E. Merck AG) and S-valerylthiophenol (a control compound synthesized by the method described in Japanese Patent Publication No. 4320/1982) were tested.

(ii) Esterases (ArE, ChE)

ArE used was isolated and purified from a commercial human serum (Miles Laboratories, Inc.) according to the method of S. S. Choi and T. L. Forster [cf. J. Dairy Sci., 50, 1088 (1967)]. ChE used was that produced by Boehringer Mannheim GmbH (derived from human plasma).

(iii) Method

The rates of hydrolysis of the test compounds with ArE and ChE were measured by the following methods.

(1) Compounds of the invention obtained in Examples 1 to 14

The rates of hydrolysis of the compounds of this invention were measured according to the method of G. L. Ellman et al. [cf. Biochem. Pharm., 7, 88 (1961)] as follows:

(1a) Compounds obtained in Examples 1 to 10

One hundred microliters of an esterase solution was added to 100 microliters of a 3.2 mM solution of DTNB and 800 microliters of a 0.4 mM solution of each of the compounds of the invention (for a compound of Example 10, a 4.0 mM solution was used). The mixture was maintained at 25° C., and an increase in absorbance at 412 nm per minute ($\Delta OD_{412}$/min) was measured by a spectrophotometer equipped with a self-recorder. The rate of hydrolysis (micromoles/ml/min) was calculated from the following equation.

$$\text{Rate of hydrolysis} = \frac{\Delta OD_{412}/\text{min.}}{13.6}$$

The DTNB and esterase solutions were prepared by using a 50 mM PIPES-sodium hydroxide buffer (Good's buffer, pH 6.5) containing 8 mM $CaCl_2$ and 0.08 mM EDTA.2Na. The solution of each compounds of this invention obtained in Examples 1 to 9 was prepared by diluting its 20 mM dimethyl sulfoxide (DMSO) solution (a 200 mM DMSO solution was used for the compound of Example 10) with the Good's buffer containing the above salts to 50 times.

The esterase was added so that its concentration was 1 unit/ml in the final dilution. The esterase unit was determined by the following method. For ArE, the amount of ArE which forms 1 micromole of phenol per minute at 25° C. using phenyl acetate as a substrate was measured and defined as one unit by the method of W. Junge and H. Klees. For ChE, the amount of ChE which forms 1 micromole of thiocholine per minute at 25° C. using S-butyrylthiocholine iodide as a substrate was defined as one unit by the method of G. L. Ellman cited above.

(1-b) Compounds of Examples 11 to 14

One hundred microliters of the esterase solution was added to 100 microliters of a 3.2 mM DTNB solution and 800 microliters of a 4.0 mM solution of each of the compounds obtained in Examples 11 to 14, and then the rate of hydrolysis was determined as in (1-a) above.

The DTNB solution, the solution of the compound of the invention and the esterase solution were prepared by using a 100 mM PIPES-sodium hydroxide buffer (Good's buffer, pH 6.5) containing 8 mM $CaCl_2$ and 0.08 mM EDTA.2Na.

(2) Phenyl acetate, β-naphthyl acetate and S-valerylthiophenol (control compounds)

The rates of hydrolysis of these control compounds were determined by the methods described in the literature.

Specifically, the method of W. Junge and H. Klees (cf. H. U. Bergmeyer ed., Methods of Enzymatic Analysis, 3rd edition, Verlag Chemie, Weinheim, pages 8-14, 1984) was used for phenyl acetate. The method of A. Burlina and L. Galzigna [cf. Clin. Chim. Acta, 39, 255 (1972)] was used for β-naphthyl acetate. The method described in Japanese Patent Publication No. 4320/1982 was used for S-valerylthiophenol.

(iii) Results

The results obtained are shown in Table 1.

TABLE 1

[Structure: R¹C=C(CH₂S-Ar)-O-C(=O)-O cyclic, where Ar is a phenyl ring with substituents R², R³, R⁴, R⁵, R⁶]

| Example | R¹ | Test compound (substrate) Ar (R²,R³,R⁴,R⁵,R⁶) | Concentration of the substrate (mM) | Hydrolysis rate of substrate (μ mol/ml/min) Aryl esterase (EC 3.1.1.2) | Chloline esterase (EC. 3.1.1.8) |
|---|---|---|---|---|---|
| 1 | —CH₃ | 4-F-phenyl | 0.32 | 0.387 | <10⁻³ |
| 2 | —CH₃ | 4-Cl-phenyl | " | 0.423 | <10⁻³ |
| 3 | —CH₃ | phenyl | " | 0.385 | <10⁻³ |
| 4 | —CH₃ | 4-NO₂-phenyl | " | 0.437 | <10⁻³ |
| 5 | —CH₃ | 4-CH₃-phenyl | " | 0.223 | <10⁻³ |
| 6 | —CH₃ | 4-OCH₃-phenyl | " | 0.247 | <10⁻³ |
| 7 | —H | 4-F-phenyl | " | 0.258 | <10⁻³ |
| 8 | —H | phenyl | " | 0.280 | <10⁻³ |
| 9 | —H | 4-NO₂-phenyl | " | 0.349 | <10⁻³ |
| 10 | —CH₃ | 2-Cl-3-COOH-phenyl | 3.20 | 0.111 | <10⁻³ |

Note: All $10^{-3}$ values shown as $<10^{-3}$.

TABLE 1-continued

[Structure: R¹C=C(CH₂S-aryl with R²,R³,R⁴,R⁵,R⁶) with O-C(=O)-O ring]

| Example | R¹ | Aryl group (R²-R⁶ substituted phenyl) | Concentration of the substrate (mM) | Hydrolysis rate of substrate ($\mu$ mol/ml/min) Aryl esterase (EC 3.1.1.2) | Chloline esterase (EC. 3.1.1.8) |
|---|---|---|---|---|---|
| 11 | —CH₃ | 2-SO₃Na phenyl | " | 0.115 | $<10^{-3}$ |
| 12 | —CH₃ | 2-SO₃H phenyl | " | 0.105 | $<10^{-3}$ |
| 13 | —CH₃ | 3-SO₃Na phenyl | " | 0.335 | $<10^{-3}$ |
| 14 | —CH₃ | 4-SO₃Na phenyl | " | 0.368 | $<10^{-3}$ |
| phenyl acetate (control) | | | 4.00 | 1.000 | 0.028 |
| β-naphthyl acetate (control) | | | 0.49 | 0.190 | 0.049 |
| S—valerylthiophenol (control) | | | 0.32 | 0.019 | 0.563 |

TEST EXAMPLE 2

ArE activity of human serum (1)

ArE activity in the sera of healthy adults and liver cirrhosis patients was measured using 4-(4-fluorophenyl)thiomethyl-5-methyl-1,3-dioxol-2-one obtained in Example 1 as a substrate.

(i) Subjects

Healthy adults (19 males and 10 females totalling 29 persons, aged 28 to 72) and liver cirrhosis patients (6 males aged 48 to 78).

(ii) Method

Blood was drawn in an amount of 5 to 7 ml each from the subjects, and centrifuged (3,000 rpm, 5 minutes) in a test tube containing a serum separating agent.

The ArE activity of the obtained serum samples at 37° C. was measured under the following conditions by using an automatic blood chemistry analyzer (Hitach Model 705).

Assay parameters
Assay Code: Rate-19-24 (380-480 sec)
Sample Volume: 5 (microliters)
$R_1$ (*) Volume: 400 (microliters)
$R_2$ (**) Volume: 100 (microliters)
Wavelength 1: 546 nm
Wavelength 2: 480 nm
Standard concentration: 0
Factor: —43913

(*): $R_1$ was prepared by mixing 1 ml of 1.6 w/v % DTNB (90 v/v % DMSO solution) with 100 ml of 50 mM PIPES-NaOH buffer (Good's buffer, pH 6.5).
(**): $R_2$ was prepared by dissolving 4.6 mg of 4-(4-fluorophenyl)thiomethyl-5-methyl-1,3-dioxol-2-one in 4 ml of 90 v/v % DMSO solution, and mixing the solution with 8 ml of 20 mM Ca.acetate-0.4 mM EDA 2Na solution (pH 4.4).

(iii) Results

The results are shown in Table 2.

TABLE 2

| Number of subjects | ArE activity of serum (IU/l) [average ± standard deviation (variation coefficient)] |
|---|---|
| Healthy adults (29) | 3,208 ± 604 (19%) |
| Cirrhosis patients (6) | 1,599 ± 373 (23%) |

TEST EXAMPLE 3

ArE activity of human serum (2)

ArE activity in the sera of healthy adults and liver cirrhosis patients was measured using sodium 4-[(5-methyl-2-oxo-1,3-dioxol-4-yl)methylthio]benzenesulfonate obtained in Example 14 as a substrate.

(i) Subjects

Healthy adults (15 males and 18 females totalling 33 persons, aged 28 to 76) and liver cirrhosis patients (4 males and 2 females totalling 6 persons, aged 48 to 76).

(ii) Method

In the same way as in Test Example 2, the ArE activity of the obtained serum samples at 37° C. was measured under the following conditions by using an automatic blood chemistry analyzer (Hitach Model 705).

Assay parameters
Assay Code: Rate-19-22 (380–440 sec)
Sample Volume: 5 (microliters)
$R_1$ (*) Volume: 400 (microliters)
$R_2$ (**) Volume: 100 (microliters)
Wavelength 1: 546 nm
Wavelength 2: 480 nm
Standard concentration: 0.0
Factor: −439

(*): $R_1$ was prepared by dissolving 4 mg of DTNB in 20 ml of a 50 mM PIPES-NaOH buffer (Good's buffer, pH 6.5) containing 5 mM $CaCl_2$ and 0.05 mM EDTA.2Na.
(**): $R_2$ was prepared by dissolving 32 mg of sodium 4-(5-methyl-2-oxo-1,3-dioxol-4-yl)methylthio]-benzenesulfonate in 6 ml of purified water.

(iii) Results

The results are shown in Table 3.

TABLE 3

| Number of subjects | ArE activity of serum (IU/ml) [average ± standard deviation (variation coefficient)] |
| --- | --- |
| Healthy adults (33) | 12.7 ± 1.9 (15%) |
| Cirrhosis patients (6) | 7.0 ± 2.0 (29%) |

The following Production Examples and Examples illustrate the present invention more specifically.

PRODUCTION EXAMPLE 1

Synthesis of triethylammonium 2-mercaptobenzenesulfonate

Sodium hydroxide (4.01 g) was dissolved in 100 ml of water, and 17.32 g of 2-aminobenzenesulfonic acid was dissolved in the solution. Then, 20 ml of conc. hydrochloric acid was added. To the resulting suspension a solution of 6.90 g of sodium nitrite in 20 ml of water was gradually added at 1° to 3° C. to give the suspension of the diazonium salt. On the other hand, 3.21 g of sulfur and 24.0 g of sodium sulfide nonahydrate were co-melted and then dissolved in 100 ml of water. The suspension of the diazonium salt was added to the above solution, and the mixture was heated. After bubbling ceased, the temperature of the reaction mixture was returned to room temperature, and the insoluble materials were separated by filtration. The filtrate was concentrated to dryness, and the residue was dissolved in 200 ml of methanol. The insoluble materials were separated by filtration, and the solvent was evaporated under reduced pressure. The residue was dissolved in 120 ml of water, and 30 ml of acetic acid and 20 g of zinc were added. The insoluble materials were separated by filtration, and the reaction mixture was extracted with a mixed solvent of aniline and benzene (1/1, v/v). The solvent was evaporated under reduced pressure, and the resulting resinous product was stirred in about 150 ml of benzene. The resulting powder was collected by filtration, and crystallized from methanol to give 5.39 g of anilinium 2-mercaptobenzenesulfonate as colorless crystals.

Then, 2.0 g of the resulting anilinium 2-mercaptobenzenesulfonate was subjected to ion-exchange column chromatography (about 30 ml of Dowex 50W-X2, 100–200 mesh, H-form was filled into a column) and eluted with a mixed solvent of methanol and water (4/1, v/v). Acidic fractions were concentrated under reduced pressure, and about 50 ml of isopropanol was added to the resulting syrup. The solvent was evaporated under reduced pressure. To 1.1 g of the resulting syrup, about 4 ml of isopropanol was added to form a solution. Triethylamine (0.58 g) was added to the solution, and the resulting crystals were collected by filtration to give 0.84 g of the captioned compound as colorless crystals (melting point: 89° to 90° C.)

PRODUCTION EXAMPLE 2

Synthesis of 3-mercaptobenzenesulfonic acid

Sodium hydroxide (4.0 g) was dissolved in 300 ml of water, and 17.3 g of 3-aminobenzenesulfonic acid was dissolved in the solution. Then, 20 ml of conc. hydrochloric acid was added. To the resulting suspension a solution of 6.9 g of sodium nitrite in 20 ml of water was gradually added at 1° to 3° C. to give the suspension of the diazonium salt. On the other hand, 3.2 g of sulfur and 24.0 g of sodium sulfide nonahydrate were co-melted and dissolved in 300 ml of water. The suspension of the diazonium salt was added to the above solution, and the mixture was heated. After bubbling ceased, the temperature of the reaction mixture was returned to room temperature, and the insoluble materials were separated by filtration. The filtrate was concentrated to dryness, and a solution of 24.8 g of aniline and 22 ml of conc. hydrochloric acid in about 100 ml of water was added to the residue. The precipitated crystals were collected by filtration, and recrystallized from isopropanol to give 9.8 g of dianilinium 3,3'-dithiobis(benzenesulfonate) as colorless crystals. (A product obtained by recrystallizing these colorless crystals from methanol showed a melting point of 251° to 255° C.)

Then, 5.0 g of the resulting dianilinium 3,3'-dithiobis(benzenesulfonate) was subjected to ion-exchange column chromatography (about 23 ml of Dowex 50W-X2, 100–200 mesh, H-form was filled into a column), and eluted with a mixed solvent of methanol and water (2/1, v/v). Acidic fractions were concentrated to dryness under reduced pressure, and the residue was dissolved in 100 ml of methanol. To the solution were added 5.1 g of triphenylphosphine and about 1 ml of water, and the mixture was stirred overnight. Thereafter, the solvent was evaporated under reduced pressure, and the resulting residue was dissolved in 70 ml of dichloromethane, and extracted twice with water (100 ml, 50 ml). The aqueous layer was washed with dichloromethane (50 ml×4), and concentrated to dryness under reduced pressure. The resulting residue was dissolved in dioxane, and the insoluble materials were separated by filtration. The dioxane was then evaporated under reduced pressure. Then, the resulting residue was dissolved in ether, and the insoluble materials were separated by filtration. The ether was then evaporated to give 2.4 g of the captioned compound as a pale yellowish brown syrup.

PRODUCTION EXAMPLE 3

Synthesis of 4-mercaptobenzenesulfonic acid

Sodium hydroxide (20.0 g) was dissolved in 500 ml of water, and 86.6 g of 4-aminobenzenesulfonic acid was dissolved in the solution. Then, 100 ml of conc. hydrochloric acid was added. To the resulting suspension a solution of 34.5 g of sodium nitrite in 100 ml of water was gradually added at 1° to 3° C. to give the suspension of the diazonium salt. On the other hand, 16.0 g of sulfur and 120.1 g of sodium sulfide nonahydrate were co-melted, and dissolved in 500 ml of water. The suspension of the diazonium salt was added to the above solution, and the mixture was heated. After bubbling ceased, the temperature of the reaction mixture was returned to room temperature, and the insoluble materials were separated by filtration. A solution of 93.4 g of aniline and 84 ml of conc. hydrochloric acid in about 200 ml of water was added to the filtrate. The precipitated crystals were collected by filtration, recrystallized from water, and washed with ethanol and then with n-hexane to give 58.7 g of dianilinium 4,4'-dithiobis(benzenesulfonate) as colorless crystals. (A product obtained by recrystallizing the colorless crystals from methanol decomposed with foaming at about 280° C.)

Then, 6.0 g of dianilinium 4,4'-dithiobis(benzenesulfonate) was subjected to ion-exchange column chromatography (about 28 ml of Dowex 50W-X2, 100–200 mesh, H-form was filled into a column), and eluted with a mixed solvent of methanol and water (2/1, v/v). Acidic fractions were concentrated to dryness under reduced pressure, and the residue was dissolved in 100 ml of methanol. To the solution were added 6.1 g of triphenylphosphine and about 1 ml of water, and the mixture was stirred overnight. The solvent was then evaporated under reduced pressure. The residue was dissolved in 60 ml of dichloromethane, and extracted twice with water (100 ml, 50 ml). The aqueous layer was washed with dichloromethane (50 ml × 4), and concentrated to dryness under reduced pressure. The residue was dissolved in 50 ml of dioxane, and the insoluble materials were separated by filtration. Under reduced pressure, dioxane was evaporated, and the resulting syrup was crystallized from benzene to give 1.6 g of the captioned compound as pale orange yellow crystals (melting point: 99° to 101° C.)

EXAMPLE 1

Synthesis of 4-(4-fluorophenyl)thiomethyl-5-methyl-1,3-dioxol-2-one

In 40 ml of dichloromethane was dissolved 2.0 g of 4-chloromethyl-5-methyl-1,3-dioxol-2-one, and 1.8 g of 4-fluorobenzenethiol was added. Then, 1.4 g of triethylamine was added, and the mixture was stirred at room temperature for 30 minutes. After the reaction, the solvent was evaporated under reduced pressure. The residue was dissolved in ethyl acetate, and the insoluble materials were separated by filtration. The solvent was evaporated under reduced pressure. The residue was subjected to medium-pressure silica gel column chromatography under the conditions shown below. The eluate was evaporated under reduced pressure, and the residue was recrystallized from a mixed solvent of ethyl acetate and n-hexane to give 1.8 g of the captioned compound as pale yellow crystals.

Melting point: 60°–62° C.
IR (KBr) $\nu$ (cm$^{-1}$): 1811 (C=O), 1734 (C=C).
NMR (CDCl$_3$) $\delta$: 1.7 (s, 3H, —CH$_3$), 3.7 (s, 2H, —CH$_2$—), about 6.9–7.7 (m, 4H, aromatic protons).
Elemental analysis for C$_{11}$H$_9$O$_3$SF: Calculated (%): C, 54.99; H, 3.78. Found (%): C, 54.78; H, 3.79.

Conditons for medium-pressure silica gel column chromatography

Silica gel 60 (230–400 mesh, a product of Merck Co.) in an amount about 60 times the amount of the sample was filled in the dry state into a column for medium-pressure column chromatography, and a mixed solvent of chloroform/n-hexane (1/2, v/v) was passed through the column. Then, the sample was charged onto the prepared column, and the column was eluted under a pressure of 1 to 3 kg/cm$^2$ with a mixed solvent of chloroform and n-hexane (1/2, v/v).

EXAMPLE 2

Synthesis of 4-(4-chlorophenyl)thiomethyl-5-methyl-1,3-dioxol-2-one

In 40 ml of dichloromethane was dissolved 2.0 g of 4-chloromethyl-5-methyl-1,3-dioxol-2-one, and 2.0 g of 4-chlorobenzenethiol was added. Then, 1.4 g of triethylamine was added, and the mixture was stirred at room temperature for 30 minutes. After the reaction, the solvent was evaporated under reduced pressure, and the residue was dissolved in ethyl acetate. The insoluble materials were separated by filtration, and the solvent was evaporated under reduced pressure. The residue was subjected to medium-pressure silica gel column chromatography as in Example 1. The eluate was evaporated under reduced pressure, and the residue was recrystallized from a mixed solvent of ethyl acetate and n-hexane to give 2.9 g of the captioned compound as colorless crystals.

Melting point: 54°–57° C.
IR (KBr) $\nu$ (cm$^{-1}$): 1814 (C=O), 1804 (C=O), 1730 (C=C).
NMR (CDCl$_3$) $\delta$: 1.8 (s, 3H, —CH$_3$), 3.7 (s, 2H, —CH$_2$—), about 7.2–7.4 (4H, aromatic protons).
Elemental analysis for C$_{11}$H$_9$O$_3$SCl: Calculated (%): C, 51.47; H, 3.53. Found (%): C, 51.57; H, 3.44.

EXAMPLE 3

Synthesis of 5-methyl-4-phenylthiomethyl-1,3-dioxol-2-one

In 40 ml of dichloromethane was dissolved 2.0 g of 4-chloromethyl-5-methyl-1,3-dioxol-2-one, and 1.5 g of benzenethiol was added. Then, 1.4 g of triethylamine was added, and the mixture was stirred at room temperature for 30 minutes. After the reaction, the solvent was evaporated under reduced pressure, and the residue was dissolved in ethyl acetate. The insoluble materials were separated by filtration, and the solvent was evaporated under reduced pressure. The residue was subjected to medium-pressure silica gel column chromatography as in Example 1. The eluate was concentrated under reduced pressure to give 2.3 g of the captioned compound as a colorless liquid.

Boiling point: about b 185° C./0.1 mmHg.
IR (CDCl$_3$) $\nu$ (cm$^{-1}$) 1819 (C=O), 1733 (C=C).

NMR (CDCl$_3$) δ: 1.7 (s, 3H, —CH$_3$), 3.7 (s, 2H, —CH$_2$—), about 7.2–7.7 (m 5H, aromatic protons).

Elemental analysis for C$_{11}$H$_{10}$O$_3$S: Calculated (%): C, 59.44; H, 4.54. Found (%): C, 59.31; H, 4.47.

EXAMPLE 4

Synthesis of 4-(4-nitrophenyl)thiomethyl-5-methyl-1,3-dioxol-2-one

In 40 ml of dichloromethane was dissolved 2.0 g of 4-chloromethyl-5-methyl-1,3-dioxol-2-one, and 2.1 g of 4-nitrobenzenethiol was added. Then, 1.4 g of triethylamine was added, and the mixture was stirred at room temperature for 30 minutes. After the reaction, the solvent was evaporated. The residue was dissolved in ethyl acetate. The insoluble materials were separated by filtration, and the solvent was evaporated under reduced pressure. The residue was subjected to medium-pressure silica gel column chromatography as in Example 1. The eluate was evaporated under reduced pressure, and the residue was recrystallized from ethyl acetate to give 2.4 g of the captioned compound as yellow cyrstals.

Melting point: 80°–83° C.

IR (KBr) ν (cm$^{-1}$) 1846 (C=O), 1818 (C=O), 1733 (C=C).

NMR (CDCl$_3$) δ: 2.1 (s, 3H, —CH$_3$), 4.0 (s, 2H, —CH$_2$—), about 7.3–7.6 (2H, aromatic protons), about 8.0–8.6 (2H, aromatic protons).

Elemental analysis for C$_{11}$H$_9$NO$_5$S: Calculated (%): C, 49.44; H, 3.39; N, 5.24. Found (%): C, 49.31; H, 3.40; N, 5.25.

EXAMPLE 5

Synthesis of 4-(4-methylphenyl)thiomethyl-5-methyl-1,3-dioxol-2-one

In 40 ml of dichloromethane was diissolved 2.0 g of 4-chloromethyl-5-methyl-1,3-dioxol-2-one, and 1.7 g of 4-methylbenzenethiol was added. Then, 1.4 g of triethylamine was added, and the mixture was stirred at room temperature for 1 hour. After the reaction, the solvent was evaporated under reduced pressure. The residue was dissolved in ethyl acetate. The insoluble materials were separated by filtration, and the solvent was evaporated under reduced pressure. The residue was subjected to medium-pressure silica gel column chromatography as in Example 1. The eluate was evaporated under reduced pressure, and the residue was recrystallized from a mixed solvent of ethyl acetate and n-hexane to give 2.2 g of the captioned compound as yellow crystals.

Melting point: 57°–59° C.

IR (KBr) ν (cm$^{-1}$) 1808 (C=O), 1734 (C=C).

NMR (CDCl$_3$) δ: 1.7 (s, 3H, —CH$_3$),

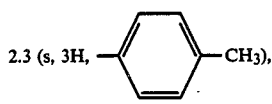

2.3 (s, 3H, —⌬—CH$_3$), 3.6 (s, 2H, —CH$_2$—), about 7.0–7.5 (m, 4H, aromatic protons).

Elemental analysis for C$_{12}$H$_{12}$O$_3$S: Calculated (%): C, 61.00; H, 5.12. Found (%): C, 60.93; H, 5.00.

EXAMPLE 6

Synthesis of 4-(4-methoxyphenyl)thiomethyl-5-methyl-1,3-dioxol-2-one

In 40 ml of dichloromethane was dissolved 2.0 g of 4-chloromethyl-5-methyl-1,3-dioxol-2-one, and 1.9 g of 4-methoxybenzenethiol was added. Then, 1.4 g of triethylamine was added, and the mixture was stirred at room temperature for 30 minutes. After the reaction, the solvent was evaporated under reduced pressure. The residue was dissolved in ethyl acetate. The insoluble materials were separated by filtration, and the solvent was evaporated under reduced pressure. The residue was subjected to medium-pressure silica gel column chromatography as in Example 1. The eluate was evaporated under reduced pressure, and the residue was recrystallized from a mixed solvent of ethyl acetate and n-hexane to give 2.3 g of the captioned compound as pale yellow crystals.

Melting point: 59°–61° C.

IR (CDCl$_3$) ν (cm$^{-1}$) 1819 (C=O), 1733 (C=C).

NMR (CDCl$_3$) δ: 1.6 (s, 3H, —CH$_3$), 3.6 (s, 2H, —CH$_2$—), 3.8 (s, 3H, —OCH$_3$), about 6.7–7.0 (2H, aromatic protons), about 7.2–7.5 (2H, aromatic protons).

Elemental analysis for C$_{12}$H$_{12}$O$_4$S: Calculated (%): C, 57.13; H, 4.80. Found (%): C, 57.01; H, 4.84.

EXAMPLE 7

Synthesis of 4-(4-fluorophenyl)thiomethyl-1,3-dioxol-2-one

In 30 ml of dichloromethane was dissolved 1.0 g of 4-bromomethyl-1,3-dioxol-2-one, and 0.8 g of 4-fluorobenzenethiol was added. Then, 0.6 g of triethylamine was added, and the mixture was stirred at room temperature for 1 hour. After the reaction, the solvent was evaporated under reduced pressure. The residue was dissolved in ethyl acetate. The insoluble materials were separated by filtration, and the solvent was evaporated under reduced pressure. The residue was subjected to medium-pressure silica gel column chromatography as in Example 1 [except that the column was eluted with a mixture of chloroform and n-hexane (2/1, v/v)]. The eluate was evaporated under reduced pressure, and the residue was recrystallized from a mixture of ethyl acetate and n-hexane to give 0.52 g of the captioned compound as pale yellow crystals.

Melting point: 57°–59° C.

IR (CDCl$_3$) ν(cm$^{-1}$): 1849 (C=O), 1819 (C=O).

NMR (CDCl$_3$) δ: 3.7 (d, 2H, —CH$_2$—), 6.7 (t, 1H, HC=C—), 6.9–7.6 (m, 4H, aromatic protons).

Elemental analysis for C$_{10}$H$_7$O$_3$SF: Calculated (%): C, 53.09; H, 3.12. Found (%): C, 52.96; H, 2.96.

EXAMPLE 8

Synthesis of 4-phenylthiomethyl-1,3-dioxol-2-one:

In 30 ml of dichloromethane was dissolved 1.0 g of 4-bromomethyl-1,3-dioxol-2-one, and 0.7 g of benzenethiol was added. Then, 0.6 g of triethylamine was added, and the mixture was stirred at room temperature for 1 hour. After the reaction, the solvent was evaporated under reduced pressure. The residue was dissolved in ethyl acetate. The isoluble materials were separated by filtration, and the residue was evaporated under reduced pressure. The residue was subjected to medium-pressure silica gel column chromatography as in Example 1 except that the column was eluted with a mixture of chloroform and n-hexane (2/1, v/v). The eluate was concentrated under reduced pressure to give 0.7 g of the captioned compound as a colorless liquid.

Boiling point: about 175° C./0.1 mmHg.
IR (CDCl$_3$) $\nu$(cm$^{-1}$): 1849 (C=O), 1817 (C=O).
NMR (CDCl$_3$) δ:3.8 (d, 2H, —CH$_2$—), 6.7 (t, 1H, 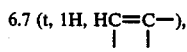), about 7.2–7.7 (m, 5H, aromatic protons).
Elemental analysis for C$_{10}$H$_8$O$_3$S: Calculated (%): C, 57.68; H, 3.87. Found (%): C, 57.54; H, 3.82.

EXAMPLE 9

Synthesis of 4-(4-nitrophenyl)thiomethyl-1,3-dioxol-2-one

In 30 ml of dichloromethane was dissolved 1.0 g of 4-bromomethyl-1,3-dioxol-2-one, and 0.9 g of 4-nitrobenzenethiol was added. Then, 0.6 g of triethylamine was added, and the mixture was stirred at room temperature for 1 hour. After the reaction, the solvent was evaporated under reduced pressure, and the residue was dissolved in ethyl acetate. The insoluble materials were separated by filtration, and the solvent was evaporated under reduced pressure. The residue was subjected to medium-pressure silica gel column chromatography as in Example 1 [except that the column was eluted with a mixture of chloroform and n-hexane (2/1, v/v)]. The eluate was evaporated under reduced pressure, and the residue was recrystallized from a mixed solvent of chloroform and n-hexane to give 0.5 g of the captioned compound as yellow crystals.

Melting point: 109°–112° C.
IR (KBr) $\nu$(cm$^{-1}$): 1870 (C=O), 1838 (C=O), 1806 (C=O), 1786 (C=C).
NMR (CDCl$_3$) δ:4.0 (d, 2H, —CH$_2$—), 6.9 (t, 1H, 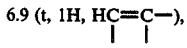), about 7.2–7.6 (2H, aromatic protons), about 8.0–8.5 (2H, aromatic protons).
Elemental analysis for C$_{10}$H$_7$NO$_5$S: Calculated (%): C, 47.43; H, 2.79; N, 5.53. Found (%): C, 47.26; H, 2.82; N, 5.57.

EXAMPLE 10

Synthesis of 2-chloro-5-[(5-methyl-2-oxo-1,3-dioxol-4-yl)methylthio]benzoic acid In 80 ml of dichloromethane was dissolved 4.0 g of 4-chloromethyl-5-methyl-1,3-dioxol-2-one, and 5.1 g of 2-chloro-5-mercaptobenzoic acid (synthesized in accordance with the method described in Swiss Pat. No. 426,865, C.A. 68.P68728c (1968)] was added. Then, 5.6 g of triethylamine was added, and the mixture was stirred at room temperature for 1 hour. After the reaction, the solvent was evaporated under reduced pressure, and the residue was subjected to medium-pressure silica gel column chromatography as in Example 1 [except that the column was prepared by using chloroform/methanol (10/1, v/v)]. Fractions of the main product obtained were concentrated to dryness under reduced pressure and the residue was dissolved in chroroform, and shaken with dilute hydrochloric acid. The chloroform layer was concentrated to dryness under reduced pressure, and then the residue was recrystallized from ethanol to give 4.8 g of the captioned compound as colorless crystals.

Melting point: 162°–164° C.
IR (KBr) $\nu$(cm$^1$) 1814 (C=O), 1800 (C=O), 1738 (C=C).
NMR (DMSO-d$_6$) δ:1.9 (s, 3H, —CH$_3$), 4.2 (s, 2H, —CH$_2$—), 7.4–7.9 (m, 3H, aromatic protons).
Elemental analysis for C$_{12}$H$_9$O$_5$SCl: Calculated (%): C, 47.93; H, 3.02. Found (%): C, 48.09; H, 2.84.

EXAMPLE 11

Synthesis of sodium 2-[(5-methyl-2-oxo-1,3-dioxol-4-yl)methylthio]benzenesulfonate In 10 ml of dichloromethane was dissolved 360 mg of 4-chloromethyl-5-methyl-1,3-dioxol-2-one, and 630 mg of triethylammonium 2-mercaptobenzenesulfonate prepared by the method of Production Example 1 was added. Then, 220 mg of triethylamine was added, and the mixture was stirred at room temperature for 2 hours. After the reaction, the solvent was evaporated under reduced pressure. Water (30 ml) was added to the residue, and the mixture was washed with 10 ml of ethyl acetate. The aqueous layer was subjected to ion-exchange column chromatography (about 10 ml of Dowex 50W-X2, 100–200 mesh, H-form was filled into a column). The column was eluted with water, and acidic fractions were concentrated under reduced pressure to a volume of about 15 ml, and saturated with sodium chloride. The precipitated colorless solid was collected by filtration, dried under reduced pressure, and then recrystallized from ethanol to give 360 mg of the captioned compound as colorless crystals.

Melting point: Began to melt and decompose gradually at about 110° C.
NMR (DMSO-d$_6$) δ:1.8 (s, 3H, —CH$_3$), 4.1 (s, 2H, —CH$_2$—), 7.1–8.0 (m, 4H, aromatic protons).
Elemental analysis for C$_{11}$H$_9$O$_6$S$_2$Na.½H$_2$O: Calculated (%): C, 39,64; H, 3.02. Found (%): C, 39.69; H, 3.09.

EXAMPLE 12

Synthesis of 2-[(5-methyl-2-oxo-1,3-dioxol-4-yl)methylthio]benzenesulfonic acid

A sodium salt of the captioned compound (500 mg) obtained in the same way as in Example 11 was dissolved in ml of water, and the solution was subjected to ion-exchange column chromatography (about 10 ml of Dowex 50W-X2, 100–200 mesh, H-form was filled into a column) and eluted with water. Acidic fractions were concentrated to dryness under reduced pressure, and the residue was washed with cyclohexane to give 430 mg of the captioned compound as a colorless crystalline powder.

Melting point: Began to color gradually at about 11020 C., and decomposed with foaming at about 130° C.

IR (KBr) $\nu$ (cm$^{-1}$) 1820 (C=O), 1740 (C=C).

NMR (DMSO-d$_6$) δ:1.8 (s, 3H, —CH$_3$), 4.1 (s, 2H, —CH$_2$—), 7.2–8.0 (m, 4H, aromatic protons).

Elemental analysis for C$_{11}$H$_{10}$O$_6$S$_2$.½H$_2$O: Calculated (%): C, 42.44; H, 3.56. Found (%): C, 42.47; H, 3.66.

EXAMPLE 13

Synthesis of sodium 3-[(5-methyl-2-oxo-1,3-dioxol-4-yl)methylthio]benzenesulfonate In 20 ml of dichloromethane was dissolved 2.2 g of 3-mercaptobenzenesulfonic acid synthesized by the method of Production Example 2, and 2.4 g of triethylamine was added. Then, a solution of 1.9 g of 4-chloromethyl-5-methyl-1,3-dioxol-2-one in 4 ml of dichloromethane was added, and the mixture was stirred at room temperature for 2.5 hours. After the reaction, the solvent was evaporated under reduced pressure. Water (60 ml) was added to the residue, and the mixture was washed with 40 ml of ethyl acetate. The aqueous layer was subjected to ion-exchange column chromatography (about 30 ml of Dowex 50W-X2, 100–200 mesh, Na-form was filled into a column) and eluted with water. Thallium acetate (20 g) was added to about 140 ml of fractions of the main product, and the mixture was left to stand overnight at about 4° C. The insoluble materials were separated by filtration, and the filtrate was concentrated under reduced presssure to about 14 ml. The precipitated colorless solid was collected by filtration, dissolved in about 120 ml of water, and concentrated under reduced pressure to precipitate crystals. This operation was repeated to give 2 g of colorless crystals. The crystals were subjected to ion-exchange column chromatography (about 8 ml of Dowex 50W-X2, 100–200 mesh, Na-form was filled into a column) and eluted with water. Fractions of the main product were concentrated to dryness under reduced pressure. The residue was dried under reduced pressure, and then recrystallized from ethanol to give 1.1 g of the captioned compound as colorless crystals.

Melting point: Decomposed with foaming gradually at about 190° C.

NMR (DMSO-d$_6$) δ:1.9 (s, 3H, —CH$_3$), 4.1 (s, 2H, —CH$_2$—), 7.2–7.7 (m, 4H, aromatic protons).

Elemental analysis for C$_{11}$H$_9$O$_6$S$_2$Na.½H$_2$O: Calculated (%): C, 39.64; H, 3.02. Found (%): C, 39.91; H, 2.98.

EXAMPLE 14

Synthesis of sodium 4-[(5-methyl-2-oxo-1,3-dioxol-4-yl)methylthio]benzenesulfonate In 20 ml of dichloromethane was dissolved 0.4 g of 4-chloromethyl-5-methyl-1,3-dioxol-2-one, and 0.5 g of 4-mercaptobenzenesulfonic acid prepared by the method of Production Example 3 was added. Then, 0.5 g of triethylamine was added, and the mixture was stirred at room temperature for 3 hours. After the reaction, the reaction mixture was worked up in accordance with the procedure described in Example 11 to give 510 mg of the captioned compound as colorless crystals.

Melting point: Began to color gradually at about 260° C. and decomposed.

NMR (DMSO-d$_6$) δ:1.85 (s, 3H, —CH$_3$), 4.1 (s, 2H, —CH$_2$—), 7.2–7.7 (m, 4H, aromatic protons).

Elemental analysis for C$_{11}$H$_9$O$_6$S$_2$Na.½H$_2$O: Calculated (%): C, 39.64; H, 3.02. Found (%): C, 39.64; H, 2.96.

What we claim is:

1. A 1,3-dioxol-2-one derivative represented by the following formula (I)

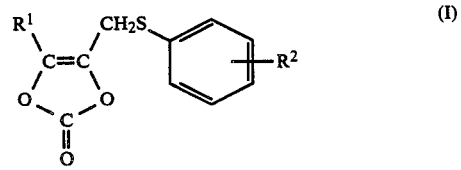

wherein
R$^1$ represents a member selected from the group consisting of a hydrogen atom or an alkyl group having 1 to 4 carbon atoms,
R$^2$ represents a hydrogen atom, a halogen atom, an alkyl group having 1 to 4 carbon atoms, an alkoxy group having 1 to 4 carbon atoms, a nitro group, a carboxyl group, a salt of the carboxyl group, a sulfo group and a salt of the sulfo group.

* * * * *